United States Patent [19]

Kanner et al.

[11] Patent Number: 4,956,156
[45] Date of Patent: Sep. 11, 1990

[54] PRESSURE VENTING SYSTEM FOR LENS CASES

[75] Inventors: Rowland W. Kanner, Guntersville; Fred E. Williams, Jr., Arab, both of Ala.

[73] Assignee: Ryder International Corporation, Arab, Ala.

[21] Appl. No.: 268,053

[22] Filed: Nov. 7, 1988

[51] Int. Cl.⁵ .............................................. A61L 2/18
[52] U.S. Cl. ...................................... 422/300; 422/301; 422/310; 220/203; 220/367; 220/373; 206/5.1; 206/438; 55/385 C; 55/385.4
[58] Field of Search ............... 422/113, 300, 301, 112, 422/310, 30; 220/366, 202, 367, 203, 373; 206/438, 5.1; 55/385 C

[56] References Cited

U.S. PATENT DOCUMENTS

| | | | |
|---|---|---|---|
| 4,396,583 | 8/1983 | Le Boeuf | 422/301 |
| 4,457,327 | 7/1984 | Pepper | 422/112 X |
| 4,469,237 | 9/1984 | Zerdian et al. | 220/366 X |
| 4,637,919 | 1/1987 | Ryder et al. | 422/300 |
| 4,750,610 | 6/1988 | Ryder | 422/300 X |

Primary Examiner—Christine M. Nucker
Assistant Examiner—Lynn M. Kummert
Attorney, Agent, or Firm—R. A. Giangiori

[57] ABSTRACT

An appliance for disinfecting contact lenses wherein the lenses are disposed within a lens disinfecting solution which produces a gas during the disinfecting action. The appliance has a container body with a lens holder for supporting a pair of contact lenses within the container and a removable cap with a vent means which seals the container to prevent contamination while permitting the venting of gases developed during the disinfecting action. The vent consists of a post positioned in a bore such that the post does not obstruct passage of gas from the inside of the container through the bore and a resiliently deflectable apertured diaphragm through which the post protrudes. The aperture in the diaphragm deflects away from the post when the pressure within the container exceeds a threshold pressure. Once the pressure within the container is equalized with the ambience, the diaphragm resiliently deflects to close the vent thereby protecting the contents of the container from contamination. Additionally, the apertured diaphragm scrapes small particles of proteinaceous material and other matter off of the post. Such matter is deposited on the post by the exhausting gas and, if not for the scraping action, would build up on the post rendering the vent useless.

16 Claims, 1 Drawing Sheet

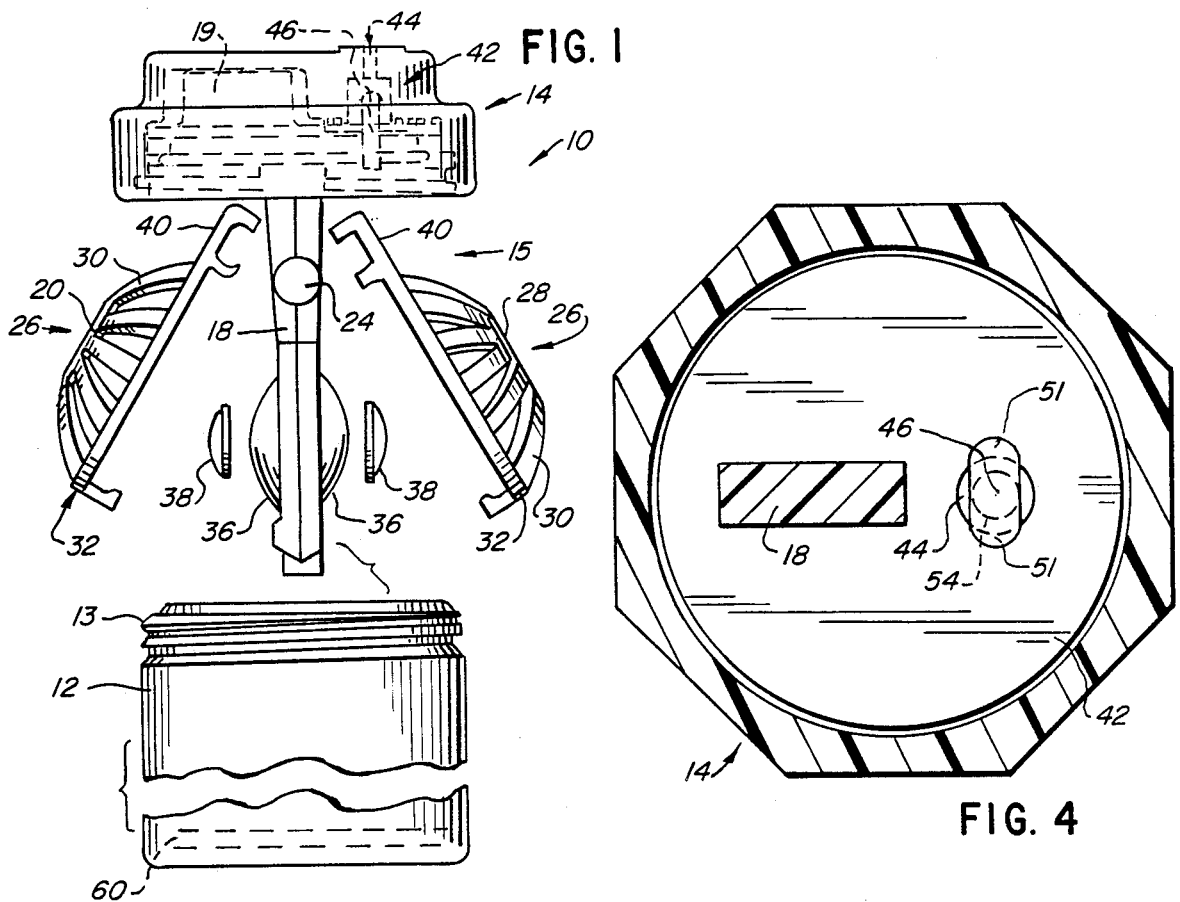
FIG. 1
FIG. 4
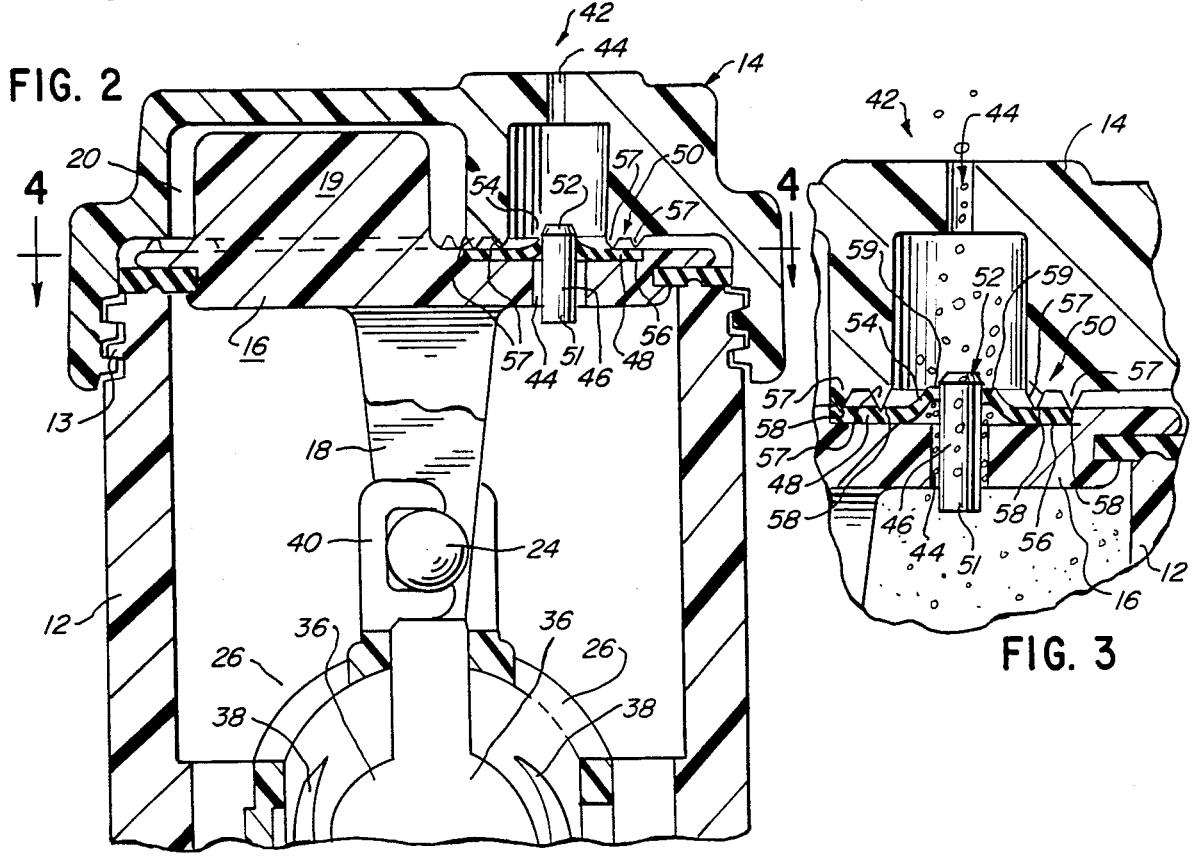
FIG. 2
FIG. 3

PRESSURE VENTING SYSTEM FOR LENS CASES

BACKGROUND OF THE INVENTION

This invention relates to an improved appliance utilized for the cleansing and/or chemical sterilization or disinfecting of small articles such as soft contact lenses.

In recent years extremely soft contact lenses have been fabricated from pliable plastic material which allow extended wear without discomfort. These plastics are hydrophilic, and for that reason contact lenses manufactured from this material are susceptible to contamination by microorganisms. Additionally, as is common with all contact lenses, during use these soft contact lenses develop a natural build-up of proteinaceous material, however, this build-up is worsened by the extended wear of these lenses. Consequently, the user of these lenses must not only disinfect and/or sterilize the lenses, generally on a daily basis to remove the build up of microorganisms, but also effect a cleaning to remove the build-up of proteinaceous material. Failure to properly clean the lenses may lead to congestion of the lens pores causing clouding of the lenses resulting in reduced visibility. Failure to disinfect or sterilize the lenses can lead to infections of the eye.

Various disinfecting techniques are used which heat the lenses in a closed vessel in the presence of a saline solution, the heat being of such intensity and duration as to destroy the contaminating microorganism. More recently, however, sterilizing processes have been developed that do not require heating. These processes utilize a bactericide, for example hydrogen peroxide, which destroys the bacteria on the lenses. In this "cold sterilization" type process, the lenses are immersed in a weak solution of hydrogen peroxide, generally a 3% solution, for several hours. While hydrogen peroxide is an effective bactericide, it is also capable of causing discomfort or injury to a wearer's eye. Therefore, in order to convert the hydrogen peroxide to a benign substance after sterilization is attained, a platinum catalyst is placed in contact with the solution to hasten the decomposition of the hydrogen peroxide, which decomposes to water and oxygen gas.

A problem with this disinfecting process is that if a bactericide such as hydrogen peroxide is used, care must be taken to preclude the possibility of discomfort or injury to the wearer's eye by sufficiently neutralizing the disinfecting agent. Accordingly, the lenses are kept in the bactericide solution for a sufficient length of time to destroy all of the bacteria, after which the lenses may be introduced into a rinsing solution to rinse out excess bactericide. Several hours is generally required to destroy essentially all of the bacteria and neutralize the hydrogen peroxide.

A problem encountered with the foregoing process is that the liberated oxygen gas results in a buildup of gas pressure within the sterilizing chamber and tends to cause leaking, spillage or both upon opening the chamber or when the cap of the unit is not sealed properly. In this regard, when the hydrogen peroxide is brought into contact with the platinum catalyst, the hydrogen peroxide solution tends to break down into water and liberated oxygen gas. The build up of liberated oxygen within the vessel creates pressure which must be vented.

To overcome the problem of cleaning the lenses of the proteinaceous material, certain protein destroying enzymes also have been added to the sterilizing solution. As these enzymes work, the enzymes and the proteinaceous material result in small particles being held in suspension with the liberated oxygen gas that must be vented. Thus a venting system is needed which not only vents the liberated oxygen gas, but can do so and also accommodate the small particles carried by said gases. Further, this must be done in a manner which maintains the sterile integrity of the lens case; that is, prevents the entry of bacteria into the case from the external environment.

In U.S. Pat. No. 4,011,941, there is shown and described a contact lens sterilizer for use with hydrogen peroxide and in which the oxygen gas pressure is relieved by displacing a rubber O-ring. Thus, the O-ring normally seals the unit, but also functions as a check valve. However, when the valve is "open", there is still the possibility of solution leaking therethrough. Moreover, an O-ring can lose resiliency over a period of time causing improper or ineffective valve operation. Further, the O-ring does not readily conform to irregularities in the seating structure and can become displaced leaving small openings through which bacteria may enter.

Additionally, the small particles of the proteinaceous material and other matter removed from the contact lenses are carried by the exhaust gas out of the lens case. When gas is exhausted there is a tendency for proteinaceous material and other particles to be deposited and build up on the valve seating area, thereby creating irregularities which increase the likelihood of bacteria propagation. Not only does the O-ring valve not conform to irregularities due to the deposits on the valve, but it is also incapable of removing these deposits. Thus, over a period of time, the O-ring type vent valve is rendered useless since it does not have means to remove built up deposits.

In U.S. Pat. No. 4,637,919, which is incorporated herein by reference, an appliance is described for disinfecting contact lenses or the like which employs a hydrophobic membrane filter that continuously vents the buildup of gas within the unit during the disinfecting process, while at the same time keeping the unit effectively sealed against leakage of disinfecting solution and entrance of bacteria into the sterilizing chamber. The membrane filter, while effective in venting oxygen gas and preventing the entry of bacteria, is susceptible to clogging when the sterilization solution includes enzymes for cleaning the lenses. The small particles carried by the liberated oxygen gas will be deposited upon the membrane during venting, and the membrane will soon become blocked and cease to function as a vent.

The present invention, as will be detailed more fully hereinafter, overcomes the above described problem. More specifically, the present invention provides an improved venting system that permits oxygen gas to be vented, is not susceptible to clogging, and prevents the entry of bacteria from the exterior of the lens case.

SUMMARY OF THE INVENTION

The present invention comprises an appliance for disinfecting contact lenses or the like wherein said lenses are disposed within a lens disinfecting solution which produces a gas during the disinfecting action. Basically, said appliance comprises a container having a body with an open end, lens holder means for supporting a pair of contact lenses being disposed within said container body, a removable cap member for closing said container open end when assembled, said cap member and said container forming a closed chamber. A bore in said cap member provides a passage from inside said closed chamber to the outside of said closed chamber. Venting means for sealing said bore against the entry of contaminants yet permitting the escape of gases developed during the disinfecting action is also employed. Said venting means comprises a post member positioned in said bore such that said post member does not obstruct passage of gas from the inside of said container. A resiliently deflectable apertured diaphragm covers said bore and is securely held in place over and around said post member with said post member protruding through said diaphragm. Said diaphragm is deflected by the buildup of gas inside the container to permit said gas to be vented to the atmosphere. The diaphragm movement also tends to wipe the post and keep it clean and free of material.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like reference numerals identify like elements, and in which:

FIG. 1 is an exploded partial elevational view of a lens disinfecting appliance;

FIG. 2 is an enlarged, partial sectional view of the assembled container cap and upper body portion of the container body shown in FIG. 1;

FIG. 3 is an enlarged partial sectional view of the vent means of the invention illustrating passage of gas through an opened post through diaphragm valve; and FIG. 4 is a sectional view taken along line 4—4 in FIG. 2 and viewed in the direction indicated illustrating the position and structure of the post member in the removable cap member.

It should be noted that dimensional relationships between members of the illustrated embodiment may vary and may have been varied to more clearly depict the features of the illustrated embodiment.

DETAILED DESCRIPTION OF THE ILLUSTRATED EMBODIMENT

While this invention is susceptible to embodiment in many different forms, there is shown in the drawings, and will herein be described in detail, one specific embodiment with understanding that the present disclosure is to be considered an exemplification of the principals of the invention, and it is not intended to limit the invention to the embodiment illustrated.

FIG. 1 shows a lens case 10 which is used to contain a solution into which contact lenses are disposed for the purpose of disinfecting and/or cleaning. To facilitate the cleaning, the lens case 10 comprises a container 12 for receiving the solution in which the lenses are disposed, with a generally cylindrical body having an opening around which are formed threads 13 for receiving a removable cap member 14. The container 12 and removable cap member 14 are molded from a suitable plastic material or the like. Mounted in the removable cap member 14 is a contact lens retaining means 15, which allows the contact lenses to be captively disposed within the solution in the container 12.

The contact lens retaining means 15 is comprised of a disc or base 16 and a lens supporting frame 18. As best shown in FIGS. 2 and 4, the surface of the disc 16 which abuts the inside of the cap member 14, has an upstanding tongue 19 which fits into an aligning mortise 20 formed in the cap 14. In an alternative embodiment of the removable cap member 14, the cap member 14, disc 16 and supporting frame 18 are integrally formed of plastic or other suitable material.

The supporting frame 18, which is integrally molded with the disc 16, projects downwardly into the container 12 when the cap 14 is mounted thereon. Integrally molded on the frame 18 are opposed, axially aligned trunions or pins 24. Opposed lens or object covers 26 are mounted on the pins 24. Each cover has an end piece 28 and a series of spokes 30 radiating therefrom and being joined to their respective rims 32. A pair of flexible snap fingers 34 are formed at the distal end of each cover 26 which allow the covers 26 to snap fit over the pins 24 when the covers 26 are hingedly attached to the pins 24. When so mounted, each cover 26 is capable of independently hingedly moving about the pins 24 to captively hold objects to be disposed in the solution in the container 12.

A special lens or object securing or mounting structure 36 has been integrally formed with the supporting frame 18 to complement the captive holding characteristics of the covers 26. This object securing structure 36 is comprised of outwardly facing convex button-like structures positioned on opposed sides of the supporting frame 18. These structures 36 are formed to receive the concave surface of contact lenses 38. The complementary operational design of the structure 36 receiving the concave portion of the lenses 38 and the concave structure of the covers 26, act to captively suspend the contact lenses 38 once disposed in the solution within the container 12. Additionally, the button-like structure forming the convex object securing structure 36 is suspended within the supporting frame 18 by a series of ribs 40 (not shown) to permit the passage of fluid through the object securing structure 36.

Similarly, an alternative embodiment may provide a structure for fixing or otherwise holding items other than contact lenses 38 for insertion into a suitably sized container in a manner as previously described.

As best shown in FIGS. 2 and 4, the cap member 14 comprises vent means 42 which permits the exhausting of gas developed within the lens case 10. The vent means 42 comprises a bore 44, a post member 46, an apertured diaphragm 48 and diaphragm compressing means 50. The post member 46 projects through the bore 44 and is secured in parallel alignment with the bore 44 by tab means 51. In the illustrated embodiment, the tab means 51 are integrally formed on one end of the post member 46 extending outwardly from the axis of the post 46 and are secured to the inside facing surface of the disk 16 on the edge of the bore 44. The post member 46 of the illustrated embodiment is a solid cylindrical pin structure, with an outside diameter dimension being less than the inside diameter dimension of the bore 44 through which it protrudes. Additionally, the top end of the post member 46 is formed with a taper feature 52 to promote the directional biasing of the diaphragm 48. Thus constructed and positioned, the post member 46 provides a structural element of the vent means 42 without obstructing the flow of gas out of the lens case 10.

The diaphragm 48 which is circular-shaped and constructed of resiliently deflectable material having a substantially concentric aperture 54 therethrough, is stretched over the post member 46 resulting in the aperture 55 in the diaphragm 48 tightly sealing around the post member 46. The degree of tightness of the seal created by the diaphragm 48 being stretched over the post member 46 is controlled by such factors as the diameter of the post member 46, the diameter of the bore 44, the diameter of the aperture 54 and the characteristics of the material of the diaphragm 48.

A supporting seat feature 56 is formed on the surface of the disc 16, which abuts the inside of the cap member 14, being generally concentric with the bore 44 through which the post member 46 protrudes. In the illustrated embodiment, the supporting seat feature 56 is generally circular, with a diameter approximately equal to the outside diameter of the diaphragm 48. The diaphragm 48 is secured in the seat feature 56 by diaphragm compressing means 50, which compress the diaphragm between this structure and the supporting seat feature 56.

The diaphragm compressing means 50 comprises two rings 57 integrally formed in the cap member 14 generally concentric with the bore 44. In the illustrated embodiment the rings 57 are generally formed with a triangular cross-section, whereby the point 58 of the ring 57 presses into the diaphragm material 48 to securely hold the diaphragm in the supporting seat feature 56.

As a result of stretching the aperture 54 of the resilient diaphragm material 48 over the post member 46, and securely holding the perimeter of the diaphragm 48 in the seat feature 56 by diaphragm compressing means 50, the aperture 54 portion of the diaphragm 48 is upwardly directionally biased. This directional biasing of the diaphragm 48 up around the post member 46 provides vent means 42 which permit exhausting of gas, but will not permit external gases and contaminants to enter the lens case 10.

When the pressure within the container 12 of the illustrated embodiment exceeds a specified threshold pressure, for example above 75 psig, the diaphgragm 48 resiliently deflects away from the post member 46 thereby opening the vent means 42 to allow passage of gas. The excessive pressure is relieved by the passage of gas from the inside of the lens case through the bore 44, past the post 46, through the resiliently deflected aperture 54 in the diaphragm 48 and out through the remainder of the bore 44 in the cap member 14. The flow path of the gas is illustrated by the arrows in FIG. 3. When the pressure inside the lens case 10 is reduced below the pressure necessary to deflect the diaphragm 48, the diaphragm will resiliently deflect downwardly in an upwardly biased orientation, with the aperture 54 of the diaphragm 48 sealing around the post member 46.

In the illustrated embodiment, repeated opening and disclosing of the vent means 42 provides the primary venting of gas throughout the disinfecting process, thereby allowing the release of gas while sealing the container against contamination. In an alternative embodiment, the diaphragm 48 is constructed of a resiliently deflectable gas-permeable hydrophobic material, such that below a specified threshold pressure required to deflect the diaphragm 48, gas is permitted to escape from the lens case 10 through microscopic pores in the diaphragm 48.

The diaphragm 48, while preventing bacteria and other contaminants from entering the lens case 10, also prevents small particles of proteinaceous material and other matter from building up on the post member 46. During the disinfecting process, small particles of proteinaceous material and other matter are removed from the contact lenses and suspended in solution. When the gas builds up inside the lens case 10 and is subsequently vented through the vent means 42, a portion of the small particles of proteinaceous material and other matter are liberated with the gas and tend to be deposited on the post member 46 while being transported through the exhaust bore 44. Since the aperture 54 of the resiliently deflectable diaphragm 48 is stretched over the post member 46, constricting forces are created by the stretched diaphragm aperture 54 on the post member 46. These constricting forces combine with the downward resilient deflection of the diaphragm 48 after the pressure within the chamber has been decreased below a threshold pressure, creating a highly effective scraping action. This scraping action is very important to the successful operation of the vent means 42 since without the scraping action, matter deposited on the post member 46 would build up and render the vent means 42 useless. The scraping action can be further enhanced by die-cutting the leading edge 59 of aperture 54. An alternative embodiment used to enhance the scraping action employs a sharp hard material implanted along the leading edge 59 of the diaphragm 48 of the aperture 54.

In use, the contact lenses 38 are placed against the button-like structures 36 of the lens-supporting frame 18 and the covers 26 are then closed over the lenses 38 to secure the lenses 38 for disinfecting and cleansing. An appropriate disinfecting and cleaning solution is poured into the open end of the container 12 and, in addition, a catalyst 60 may then be introduced to the solution if prescribed by the particular disinfecting procedure. The lens supporting structure 18, with the captive lenses 38 is disposed within the solution in the container 12, and then the container 12 is sealed by tightening the cap member 14 about the threads 13 on the open end of the container 12. The lenses 38 in the solution, as such, are left to the disinfecting process for a suitable length of time. During the disinfecting process gas is liberated from the solution which builds up pressure inside the lens case 10. When the pressure exceeds a specified threshold pressure, the diaphragm 48 resiliently deflects away from the post member 46 to open the vent means 42, thereby exhausting the excess pressurized gas. By venting the gas, the pressure within the lens case 10 is relieved, and when this pressure is substantially equalized with the ambience, the diaphragm 48 resiliently deflects to seal around the post member 46. While sealing around the post member 46, the constrictive forces created by the resilient diaphragm aperture 54 and the leading edge 59 of the diaphragm aperture 54, scrape any material off the post member 46 which may have been deposited by the exhausting gas. Once the disinfecting process is complete, the lenses 38 are removed from the lens case 10 and applied to the user's eyes in accordance with precribed procedures.

While particular embodiments of the present invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific instruction described herein, but should be defined in the depended claims and equivalents thereof. Accordingly, the aim in the appended claims is to cover all such changes and modifications as fall within the true spirit and scope of the invention.

The invention is claimed as follows:

1. An appliance for disinfecting contact lenses or the like wherein said lenses are disposed within a lens disinfecting solution which produces a gas during the disinfecting action, said appliance comprising: a container having a body with means defining an open end; lens holder means for supporting a pair of contact lenses being disposed within said container body; a removable cap member for closing said container open end; means defining a bore in said cap member providing a passage from an inner surface of said cap member to an outer surface of said cap member; vent means for sealing said bore against entry of contaminants yet permitting escape of gases developed during the disinfecting action, said vent means comprising: a post member positioned in said bore such that said post member does not obstruct passage of gas from inside of said container, a resiliently deflectable apertured diaphragm covering said bore and securely held in place over and around said post member and through which said post member protrudes, with said post member protruding through said diaphragm aperture such that when gas accumulates in said container and when pressure inside the container is greater than a specified threshold pressure, said resiliently deflectable diaphragm resiliently deflects to unseat from said post member to open said vent means, thereby releasing the gas; and when the pressure is relieved such that pressure inside said container is less than a specified threshold pressure, said diaphragm resiliently deflects against said post member to seat thereon and to close said vent means.

2. An appliance according to claim 1 wherein said cap means is formed with an outer cap passage connecting with said vent means and said vent means has a major axis being substantially aligned with a major axis in said outer cap passage.

3. An appliance according to claim 1, wherein said post member is a solid cylindrical pin structure, with an outside diameter being less than an inside diameter of said bore.

4. An appliance according to claim 3, wherein said post member includes tab means for affixing said post member to said cap member to support said post member in said bore.

5. An appliance according to claim 1, further comprising:
    said resiliently deflectable apertured diaphragm being mounted in a supporting seat feature; and
    said post member being tapered on an end over which said resiliently deflectable apertured diaphragm is positioned;
    whereby directional biasing of said diaphragm results when said diaphragm has an aperture with an inside diameter less than an outside diameter of said post member.

6. An appliance according to claim 5, wherein said cap member further comprises diaphragm compressing means being integrally formed with said cap member for compressing said diaphragm between said diaphragm compressing means and said seat feature to secure said diaphragm in said supporting seat feature.

7. An appliance according to claim 1, wherein said diaphragm is a resiliently deflectable gas permeable hydrophobic material for venting gas through micro pores in the material whereby below a threshold pressure required to open said vent means gas is permitted to escape said container through said gas permeable material.

8. An appliance according to claim 7, wherein said diaphragm aperture has a leading edge for scraping off said post member such particles or other matter which may be deposited on the surface of said post member by exhausting gas.

9. An appliance as defined in claim 1, wherein said diaphragm aperture has a leading edge for scraping off said post member such particles or other matter which may be deposited on the surface of said post member by exhausting gas.

10. An appliance for containing objects wherein said objects are disposed within a material which produces a gas during a reaction, said appliance comprising: a container having a body with means defining an open end; an object holder means for supporting at least one object being disposed within said container body; a removable cap member closing said container open end; means defining a bore in said cap member providing a passage from an inner surface of said cap member to an outer surface of said cap member; vent means for sealing said bore below a specified threshold pressure yet permitting escape of gases above a specified threshold pressure, said vent means comprising a post member positioned in said bore such that said post member does not obstruct passage of gas from the inside of said container through said bore, a resiliently deflectable apertured diaphragm covering said bore and securely held in place over said post member with said post member protruding through said diaphragm aperture.

11. An appliance according to claim 10, wherein said diaphragm material is a resiliently deflectable gas permeable hydrophobic material.

12. An appliance for disinfecting contact lenses including a container wherein said lenses are disposed within a lens disinfecting solution which produces a gas during the disinfecting action, said appliance comprising vent means for venting liberated gas, said vent means comprising: means defining a bore leading from an interior of said container to an exterior thereof; a post member positioned in said bore such that said post member does not obstruct passage of gas from inside of said container; a resiliently deflectable apertured diaphragm covering said bore and securely held in place over and around said post member with said post member protruding through said diaphragm aperture such that when gas accumulates in said container and when pressure inside said container is greater than a specified threshold pressure, said resiliently deflectable diaphragm resiliently deflects to open said vent means thereby releasing the gas; and when the pressure is relieved, such that pressure inside said container is less than a specified threshold pressure, said diaphragm resiliently deflects against said post member to close said vent means.

13. An appliance according to claim 12, further comprising:
    said resiliently deflectable apertured diaphragm being mounted in a supporting seat feature; and
    said post member being tapered on an end over which said resiliently deflectable apertured diaphragm is positioned;
    whereby directional biasing of said diaphragm results when said diaphragm has an aperture with an inside diameter less than an outside diameter of said post member.

14. An appliance according to claim 13, wherein said cap member further comprises diaphragm compressing means being integrally formed with said cap member for compressing said diaphragm between said diaphragm compressing means and said seat feature to secure said diaphragm in said supporting seat feature.

15. An appliance according to claim 14, wherein said diaphragm aperture has a leading edge for scraping off said post member such particles or other matter which may be deposited on the surface of said post member by exhausting gas.

16. An appliance for disinfecting contact lenses wherein said lenses are disposed within a material which produces a gas during a reaction, said appliance comprising: a container having means defining a bore in said container providing a passage from the interior of said container to an outer surface thereof; vent means for sealing said bore below a specified threshold pressure yet permitting escape of gases above a specified threshold pressure, said vent means comprising a post member positioned in said bore such that gas may pass from the inside of said container through said bore, a resiliently deflectable diaphragm having an aperture formed therethrough, said post member protruding through said aperture formed in said diaphragm such that when pressure in said container exceeds said specified threshold pressure, the pressure resiliently deflectably unseats said diaphragm from said post member permitting passage of exhaust gas between an outer surface of said post member and an inner surface of said aperture formed in said diaphragm, upon equalization of the pressure inside and outside of said container said diaphragm resiliently deflects to seat said diaphragm aperture around said post member to seal said bore below said specified threshold pressure, which resilient deflection creates a wiping action by said diaphragm on said post member.

* * * * *